United States Patent [19]

Nüsslein et al.

[11] 4,239,524
[45] Dec. 16, 1980

[54] THIADIAZOLYL UREAS WITH HERBICIDAL EFFECT

[75] Inventors: Ludwig Nüsslein; Friedrich Arndt; Reinhart Rusch, all of Berlin, Fed. Rep. of Germany

[73] Assignee: Schering Aktiengesellschaft, Berlin and Bergkamen, Fed. Rep. of Germany

[21] Appl. No.: 17,135

[22] Filed: Mar. 5, 1979

Related U.S. Application Data

[63] Continuation of Ser. No. 730,570, Oct. 7, 1976, abandoned, which is a continuation of Ser. No. 624,123, Oct. 10, 1975, abandoned, which is a continuation-in-part of Ser. No. 393,598, Aug. 31, 1973, abandoned.

[51] Int. Cl.$^3$ .............................................. A01N 43/82
[52] U.S. Cl. ......................................... 71/90; 548/140
[58] Field of Search ............................................ 71/90

[56] References Cited

U.S. PATENT DOCUMENTS

| 3,951,640 | 4/1976 | Krenzer | 71/90 |
| 4,128,412 | 12/1978 | Metzger et al. | 71/90 |

FOREIGN PATENT DOCUMENTS

| 85222 | 10/1971 | Fed. Rep. of Germany | 71/90 |
| 7116163 | 5/1972 | Netherlands | 71/90 |

*Primary Examiner*—Glennon H. Hollrah
*Attorney, Agent, or Firm*—Michael J. Striker

[57] ABSTRACT

The specification discloses 5-alkylsulfonyl- and 5-alkylsulfinyl-1,3,4-thiadiazol-2-yl ureas which are characterized by a selective herbicidal activity against weeds while being innocuous against crop plants thus providing means and methods for the protection of fields of growing crops against infestation by undesirable weeds and grasses.

9 Claims, No Drawings

THIADIAZOLYL UREAS WITH HERBICIDAL EFFECT

This is a continuation of application Ser. No. 730,570, filed Oct. 7, 1976, now abandoned which in turn is a continuation of Ser. No. 624,123 filed Oct. 10, 1975 and now abandoned, which is a continuation-in-part of Ser. No. 393,598, filed Aug. 31, 1973, now abandoned.

BACKGROUND OF THE INVENTION

The instant invention relates to herbicidal agents and to methods for the prevention of weed infestation in fields of growing crop plants and more particularly to the use of herbicidal thiadiazolyl ureas as selective herbicides capable of general overall application with discriminatory results.

1,3,4-thiadiazol-2-yl ureas have been described as herbicidal substances. In this connection the best known compound is 1-methyl-1(5-trifluoromethyl-1,3,4-thiadiazol-2-yl)-3-methyl urea, cf. German Pat. No. 1,816,696. This compound, however, is not very suitable as a selective weed killer, since it does not exhibit sufficient compatibility with crop plants. From the disclosure in German Pat. No. 2,044,442, there is evidence of the herbicidal effect of alkylsulfonyl-thiadiazolyl ureas which contain an alkyl radical with 1 to 3 carbon atoms. It is to be noted, however, that these compounds do not exhibit satisfactory selectivity between crop plants and weeds.

It is therefore an object of this invention to provide compounds which are selective in toxicity against undesirable weeds and grasses as compared to agricultural crops.

Another object of the invention is to provide herbicidal composition which can be applied to fields of growing crops for the purpose of killing weeds without damage to the crops.

Another object of the invention is to provide methods for the control of weeds by either pre-emergent or post-emergent application of certain alkylsulfonyl- and alkylsulfinyl-1,3,4-thiadiazolyl ureas.

Another object of the invention is to provide means and methods for control of weed growth among growing crops comprising indiscriminate application of herbicidal compounds and composition characterized by selective toxicity.

DESCRIPTION OF THE INVENTION

These and other related objects are achieved through the provision and utilization of compounds having the formula:

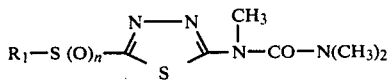

wherein $R_1$ is an alkyl radical having from 4 to 8 carbon atoms and n is an integer being either 1 or 2.

Illustrative alkyl radicals include straight and branched chain groups such as n-butyl, isobutyl, n-pentyl, n-hexyl, n-heptyl and n-octyl, tertiary butyl, secondary butyl, neopentyl, 1-methyl-butyl, 1,3,dimethyl-butyl, 1,2-dimethylpropyl, 1-ethylpropyl, and the like.

The alkylsulfonyl- and alkylsulfinyl-1,3,4-thiadiazolyl ureas described above have been found to be toxic to weeds and at such weed-killing application rates to be compatible with crop plants. Accordingly, these compounds can be employed in agricultural compositions for use in methods for the prevention of weed infestation of crop fields without damaging the crops. Such compositions are characterized by an effective content of at least one of the above described compounds.

These compounds have been found to be remarkably useful in methods for the protection of fields of growing crops against infestation by weeds. The active compound is applied to the field in a weed-killing amount. As used in this specification and claims, the term weed-killing amount is intented to mean an amount sufficient to prevent weed growth without causing substantial damage to the growing crops and therefore includes amounts which kill growing weeds or prevents germination and growth of weed seeds or seedlings. In general such a weed-killing amount is from about 0.1 to about 5 kilograms per hectare. Other useful compositions can be formulated to provide from about 1 to about 5 kilograms per hectare.

The herbicidal compounds alone or in admixture with other ingredients or carriers are applied to the field in an amount which is sufficient to kill or prevent the growth of weeds without damage to the crops. The compounds or compositions can be applied to growing weeds among the crops or to fields containing weed seed and they act through both the soil and leaf systems. The compounds are particularly effective against monocotyl and dicotyl weeds.

The compounds and compositions containing them are particularly effective against field weeds, such as Sinaris ssp., *Stellaria media, Senecio vulgaris, Natricaria chamomilla, Ipomea purpurea, Chrysanthemum segetum, Lamium amplexicaule, Centaurea cyanus, Ameranthus retroflexus myosuroides, Echinochloa crusgalli, Setaria italica, Lolium perenne* and the like.

In general effective control of weeds in fields of crops such as corn, peanuts, potatoes, soy beans, peas and other leguminosae and cereals. These compounds are also compatible with ornamental shrubs and plantings.

Effective control of weeds can be achieved by applying the active compounds at a rate of about 0.1 to about 5 kilograms per hectare. Accordingly the herbicidal compositions of the herein disclosed compounds are to be formulated to provide or deliver from about 0.1 to 5 kilograms of active compound per hectare.

The effective substances can be applied either alone or as a mixture of several substances. Also, other plant protection or pest control agents, such as fungicides, nematocides, fertilizers or other agents, depending on the desired purpose, may be added.

If an enlargement of the action spectrum or the destruction of a wasteland flora is desired, other herbicides may also be added to the formulations. For example, there can be employed substances from the group of the triazines, aminotriazoles, anilides, diazines, uracils, aliphatic carboxylic acids and halocarboxylic acids, hydrazides, amides, nitriles, esters of suca carboxylic acids, carbamic and thiocarbamic esters, ureas, 2,3,6-trichlorobenzyloxypropanol and rhodanium-containing agents and the like. In addition the formulation can include nonphytotoxic substances which result in a synergistic effect, such as wetting agents, emulsifiers, solvents and oils.

Appropriately the active ingredients can be applied in the form of preparations, such as powders, scatters, granulations, solutions, emulsions or suspensions with addition of liquid or solid vehicles or diluents and also wetting, adhesive, emulsifying or dispersing aids. Suitable liquid vehicles are water, aliphatic and aromatic hydrocarbons, such as benzene, toluene, xylene, cyclohexanone, isophorone, and also mineral oil fractions.

As solid vehicles there may be used suitable mineral earths, like siliceous clay, silica gel, talcum, kaolin, attaclay, limestone, silica, and even plant products as flours.

Among desirable surface-active substances are calcium lignin sulfonate, polyoxethylene-octyl phenol ether, naphthalene sulfonic acids, phenol sulfonic acids, formaldehyde condensates, fatty alcohol sulfates and alkali and alkaline earth salts of fatty acids. The proportion of the active compound in the formulation vary within wide limits so long as an effective amount is applied to the weeds. For example, the composition may contain about 20 to 80 percent by weight of the compound, about 80 to 20 percent by weight of a liquid or solid vehicle, and optionally up to 20 percent by weight of surfaceactive substances.

The compounds of formula (I) are produced for example by reaction of oxidizing agents with compounds of the general formula

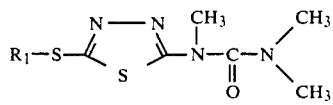

For the production of compounds of formula (I), it is possible if $n=1$, to use as oxidizers preferably organic hydro-peroxides, such as tertiary butyl hydroperoxide, or peracids, such as m-chloroperbenzoic acid, or N-halogen acid amides, such as N-bromosuccinimide, or inorganic compounds, such as hydrogen peroxide, sodium-m-periodate and the like. Advantageously, one takes for this, two oxidation equivalents of the oxidezer or a small excess per mole of the thio compounds at temperatures of about 0° to 60° C.

For the production of compounds of formula (I) with n being 2 there may be used in addition to the oxidizers above mentioned, inorganic reagents, such as chlorine or potassium permanganate, chromic acid or its salts or nitric acid, in a temperature range from about 0° to 120° C.

Per mole of the thio compound, there are taken for this approximately four oxidation equivalents or, if desired, an excess thereof, i.e. at least twice as much as for the above described sulfoxidation for the production of the defined compounds with $n=1$.

As reaction media there may be used appropriately organic solvents, such as carboxylic acids, like acetic acid, ether, like dioxane, ketones, like acetone, acid amides, like dimethylformamide, nitriles, like acetonitrile, or others, and are alone or in a mixture with water.

Compounds of the general formula (I) are arrived at moreover by reaction of compounds of the general formula

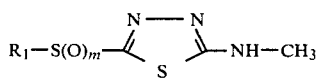

with carbamoyl halides of the general formula

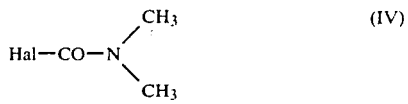

in the presence of acid-binding agents.

Another synthesis consists in the reaction of compounds of formula (III) with carbon dioxide ester halides or with phosgene in the presence of an acid-binding agent to derivatives or carbamic acid, which are then reacted with dimethylamine of the formula

to the desired process products.

Examples of carbon dioxide ester halides are carbon dioxide phenyl ester chloride and thio-carbon dioxide-S-phenyl ester chloride, obtaining therewith for example N-(5-alkylsulfonyl-1,3,4-thiadiazol-2-yl)thiocarbamic acid-S-phenyl esters, which are then reacted with dimethylamine.

In processes in which hydrohalic acid is forred, one adds for its binding organic cases tertiary amines like triethylamine, or dimethyl aniline, pyridine bases or suitable inorganic bases, like oxides and hydroxides of the alkali and alkaline earth metals.

The reaction with carbon dioxide chlorides occurs between about $-10°$ and $150°$ C., the subsequent reaction with dimethylamine of formula (V) between about $-10°$ and $100°$ C. but in general at room temperature.

Reaction media that may be used are solvents inert to the reagents. The following may be named, among others: Aliphatic and aromatic hydrocarbons and halogen hydrocarbons such as benzene, toluene, xylene, methylene chloride, chloroform, carbon tetrachloride, chlorinated amides and nitriles, and the like.

Another possible synthesis of 5-alkylsulfonyl-1,3,4-thiadiazole ureas consists in the reaction of 5-carbamoyl-amine-1,3,4-thiadiazol-2-yl sulfinic acid salts of the general formula

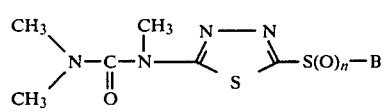

with alkylation agents of the general formula $$Hal-R_1 \quad (VII)$$

Instead of compounds of the general formula (VII), other alkylation agents may be used, namely esters of sulfuric acid or esters of aromatic sulfonic acids, such as dimethyl sulfate.

In the above mentioned general formulas II to VII, $R_1$ and n have the meaning described in the general formula I, Hal indicates chlorine, bromine or iodine, and B represents hydrogen, a univalent metal equivalent, preferably al alkali or alkaline earth metal, or a tertiary organic base.

The starting products for the execution of the described processes are known in themselves or can be produced by methods known in the art.

The following examples will illustrate the preparation of the compounds according to the invention.

EXAMPLE I 1,1,3-trimethyl-3-(5-butylsulfinyl-1,3,4-thiadiazole-2-yl)urea

To a solution of 300 g of 1,1,3-trimethyl-3-(5-butylthio-1,3,4-thiadiazol-2-yl) urea in 1.9 ltr glacial acetic acid there are added in drops at room temperature and with agitation 136 g of perhydrol. The temperature then rises to 28° C. After standing for 5 days, the perhydrol excess is destroyed with manganese dioxide, the glacial acetic acid is vacuum-distilled to a very large extent, and the residue taken up in methylene chloride, is treated twice with active carbon, the solvent distilled, and the remaining oil dried in high vacuum.

Yield: 305.5 g (96% of the theory).
$n_D^{20} = 1.5617$.

EXAMPLE 2

1,1,3-trimethyl-3-(5-butylsulfonyl-1,3,4-thiadiazole-2-yl) urea 41.1 g of 1,1,3-trimethyl-3-(5-butylthio-1,3,4-thiadiazol-2-yl) urea are dissolved in 150 ml of glacial acetic acid and 50 ml of water. Into this solution 33.6 g of finely pulverized potassium permanganate are charged between 70° and 80° C. agitation is continued for another hour, and finally one reduces the precipitated manganese dioxide in the mixture cooled to 0° C. by dropwise addition of a solution of 30 g of sodium metabisulfite in 50 ml of water. The separated oil is taken up in methylene chloride, the methylene chloride solution extracted several times with soda solution and water, the organic phase dried with magnesium sulfate, treated with active carbon, and concentrated under vacuum. The residue is recrystallized from isopropyl ether.

M.p.: 49° C.

Yield: 16.2 g (35% of the theory).

According to the methods described above other compounds listed in the following table can be produced.

| Name of Compound | Physical Constant |
| --- | --- |
| 1. 1,1,3-Trimethyl-3-(5-pentylsulfinyl-1,3,4-thiadiazol-2-yl) urea | $n_D^{20} = 1.5550$ |
| 2. 1,1,3-Trimethyl-3-(5-hexylsulfinyl-1,3,4-thiadiazol-2-yl) urea | $n_D^{20} = 1.5540$ |
| 3. 1,1,3-Trimethyl-3-(5-heptylsulfinyl-1,3,4-thiadiazol-2-yl) urea | $n_D^{20} = 1.5474$ |
| 4. 1,1,3-Trimethyl-3-(5-pentylsulfonyl-1,3,4-thiadiazol-2-yl) urea | $n_D^{20} = 1.5470$ |
| 5. 1,1,3-trimethyl-3-(5-hexylsulfonyl-1,3,4-thiadiazol-2-yl) urea | $n_D^{20} = 1.5440$ |
| 6. 1,1,3-Trimethyl-3-(5-heptylsulfonyl-1,3,4-thiadiazol-2-yl) urea | $n_D^{20} = 1.5350$ |
| 7. 1,1,3-trimethyl-3-(5-octylsulfonyl-1,3,4-thiadiazol-2-yl) urea | N.P.: 64° C. |
| 8. 1,1,3-Trimethyl-3-(5-isobutylsulfonyl-1,3,4-thiadiazol-2-yl) urea | $n_D^{20} = 1.5546$ |
| 9. 1,1,3-Trimethyl-3-(5-ethylbutylsulfonyl-1,3,4-thiadiazol-2-yl) urea | $n_D^{20} = 1.5438$ |
| 10. 1,1,3-Trimethyl-3-(5-isopentylsulfonyl-1,3,4-thiadiazol-2-yl) urea | $n_D^{20} = 1.5506$ |
| 11. 1,1,3-Trimethyl-3-(5-(1-ethylpentyl)-sulfonyl 1,3,4-thiadiazol-2-yl) urea | $n_D^{20} = 1.5422$ |
| 12. 1,1,3-Trimethyl-3-(5-(1-methylpropyl)-sulfonyl-1,3,4-thiadiazol-2-yl) urea | N.p.: 80° C. |

The compounds according to the invention are colorless and odorless, oily or crystalline substances, which are insoluble in water and gasoline and soluble in acetone, methylene chloride, tetrahydrofurane, dimethyl formamide, cyclohexanine and isophorone.

The following examples will explain the herbicidal and selective properties of the compounds according to the invention in comparison with known effective substances.

EXAMPLE 3

In the greenhouse the listed plants were treated before emergence with the agents in the stated quantities. For this purpose the agents were applied uniformly on the soil as aqueous suspensions at 500 liters/ha. The results obtained three weeks after treatment show that in contrast to the known compounds the agents according to the invention show a good selectivity.

| Agent according to invention | Quantity Used kg eff. subst./ha | A | B | C | D | E | F | G | H | I | J | K | L | M | N | O | P |
| --- | --- | --- | --- | --- | --- | --- | --- | --- | --- | --- | --- | --- | --- | --- | --- | --- | --- |
| 1. 1,1,3-Trimethyl-3-(5-butylsulfonyl-1,3,4-thiadiazol-2-yl) urea | 0.3 | 0 | 10 | — | — | 10 | — | — | — | 0 | 0 | 0 | 0 | 0 | 0 | 0 | 0 |
| 2. 1,1,3-Trimethyl-3-(5-pentylsulfonyl-1,3,4-thiadiazol-2-61) urea | 1.0 | 10 | 10 | — | — | 10 | — | — | — | 0 | 0 | 0 | 0 | 0 | 0 | 0 | 0 |
| 3. 1,1,3-Trimethyl-3-(5-hexylsulfonyl-1,3,4-thiadiazol-2-yl) urea | 3.0 | 10 | 10 | 10 | 10 | 10 | 10 | 10 | — | 0 | 0 | 0 | 0 | 0 | 0 | 0 | 0 |
| 4. 1,1,3-Trimethyl-3-(5-heptylsulfonyl-1,3,4-thiadiazol-2-yl) urea | 3.0 | 10 | — | — | — | 10 | 10 | — | — | 0 | 0 | 0 | 0 | 0 | 0 | 0 | 0 |
| 5. 1,1,3-Trimethyl-3-(5-butylsulfinyl-1,3,4-thiadiazol-2-yl) urea | 1.0 | — | 10 | — | 10 | 10 | — | — | — | 0 | 0 | 0 | 0 | 0 | 0 | 0 | 0 |
| 6. 1,1,3-Trimethyl-3-(5-pentylsulfinyl-1,3,4-thiadiazol-2-yl) urea | 1.0 | 10 | 10 | — | 10 | 10 | — | — | — | 0 | 0 | 0 | 0 | 0 | 0 | 0 | 0 |
| 7. 1,1,3-Trimethyl-3-(5-hexylsulfinyl-1,3,4-thiadiazol-2-yl) urea | 3.0 | 10 | 10 | 10 | 10 | 10 | 10 | — | 10 | 0 | 0 | 0 | 0 | 0 | 0 | 0 | 0 |
| 8. 1,1,3-Trimethyl-3-(5-isobutylsulfonyl-1,3,4-thiadiazol-2-yl) urea | 0.3 | 10 | 10 | 10 | 10 | 10 | — | — | — | 0 | 0 | 0 | 0 | 0 | 0 | 0 | 0 |
| 9. 1,1,3-Trimethyl-3-(5-ethylbutylsulfonyl-1,1,4-thiadiazol-2-yl) urea | 1 | 10 | 10 | 10 | 10 | 10 | 10 | — | — | 0 | 0 | 0 | 0 | 0 | 0 | 0 | 0 |
| 10. 1,1,3-Trimethyl-3-(5-isopentylsulfonyl-1,3,4-thiadiazol-2-yl) urea | 1 | 10 | 10 | 10 | 10 | 10 | — | — | — | 0 | 0 | 0 | 0 | 0 | 0 | 0 | 0 |
| 11. 1,1,3-Trimethyl-3-(5-(1-ethylpentyl)-sulfonyl-1,3,4-thiadiazol-2-yl) urea | 1 | 10 | 10 | 10 | 10 | 10 | 10 | — | — | 0 | 0 | 0 | 0 | 0 | 0 | 0 | 0 |
| 12. 1,1,3-Trimethyl-3-(5-(1-methylpropyl)-sulfonyl-1,3,4-thiadiazol-2-yl) urea | 0.3 | 10 | 10 | 10 | 10 | 10 | — | — | — | 0 | 0 | 0 | 0 | 0 | 0 | 0 | 0 |

-continued

| Comparison agent | Quantity used kg eff. subst./ha | A | B | C | D | E | F | G | H | I | J | K | L | M | N | O | P |
|---|---|---|---|---|---|---|---|---|---|---|---|---|---|---|---|---|---|
| 13. 1-Methyl-1-(5-trifluoromethyl-1,3,4-thiadiazol-2-yl)-3-methyl urea | 1.0 | 0 | 5 | 5 | 8 | 3 | 1 | 0 | 0 | 0 | 0 | 0 | 0 | 0 | 0 | 0 | 0 |
| 14. 1,1,3-Trimethyl-3-(5-ethylsulfonyl-1,3,4-thiadiazole-2-yl) urea | 1.0 | 0 | 4 | 0 | 3 | 5 | 0 | 0 | 0 | 0 | 0 | 0 | 0 | 0 | 0 | 0 | 0 |
| 15. 1,1,3-Trimethyl-3-(5-ethylsulfonyl-1,3,4-thiadiazol-2-yl) urea | 1.0 | 3 | 5 | 2 | 0 | 3 | 0 | 0 | 0 | 0 | 0 | 0 | 0 | 0 | 0 | 0 | 0 |
| 16. 1,1,3-Trimethyl-3-(5-n-propyl-sulfonyl-1,3,4-thiadiazol-2-yl) urea | 1.0 | 4 | 5 | 4 | — | 3 | 0 | 0 | 0 | 0 | 0 | 0 | 0 | 0 | 0 | 0 | 0 |
| 17. 1,1,3-Trimethyl-3-(5-isopropyl-sulfonyl-1,3,4-thiadiazol-2-yl) urea | 1.0 | 3 | 2 | 2 | 2 | 2 | 0 | 0 | 0 | 0 | 0 | 0 | 0 | 0 | 0 | 0 | 0 |
| 18. 1,1,3-Trimethyl-3-(5-n-propyl-sulfinyl-1,3,4-thiadiazol-2-yl) urea | 1.0 | 5 | 4 | 4 | — | 7 | 0 | 0 | 0 | 0 | 0 | 0 | 0 | 0 | 0 | 0 | 0 |
| 19. 1,1,3-Trimethyl-3-(5-isopropyl-sulfinyl-1,3,4-thiadiazol-2-yl) urea | 1.0 | 5 | 7 | 2 | 1 | 5 | 0 | 0 | 0 | 0 | 0 | 0 | 0 | 0 | 0 | 0 | 0 |
| Untreated | | 10 | 10 | 10 | 10 | 10 | 10 | 10 | 10 | 10 | 10 | 10 | 10 | 10 | 10 | 10 | 10 |

0 = totally destroyed
10 = not damaged
A = Sorghum sativum
B = Corn
C = Rice
D = Potatoes
E = Peanut
F = Soybean
G = Barley
H = Cotton
I = Stellaria media
J = Senecio vulgaris
K = Natricaria chazomilla
L = Lamimum amplexioaule
M = Centaurea cyanus
N = Amaranthus retroflexum
O = Chrisanthemum sogetum
P = Iponea purpurea

EXAMPLE 4

In the greenhouse the listed plants were treated after emergence with the agents in the stated quantities. For this purpose the agents were uniformly sprayed over the plants as aqueous suspensions at 500 liters/ha. Also, here the results obtained 3 weeks after treatment show that the agents according to the invention have a better selectivity than the comparison compounds.

| Agent according to invention | Quantity used kg eff. subst./ha | A | B | C | D | E | F | G | H | I | J | K | L | M | N | O |
|---|---|---|---|---|---|---|---|---|---|---|---|---|---|---|---|---|
| 1. 1,1,3-Trimethyl-3-(5-butylsulfonyl-1,3,4-thiadiazol-2-yl) urea | 0.3 | — | 10 | 10 | 10 | 10 | 10 | 10 | — | 0 | 0 | 0 | 0 | 0 | 0 | 0 |
| 2. 1,1,3-Trimethyl-3-(5-pentylsulfonyl-1,3,4-thiadiazol-2-yl) urea | 1.0 | 10 | 10 | 10 | 10 | 10 | — | 10 | — | 0 | 0 | 0 | 0 | 0 | 0 | 0 |
| 3. 1,1,3-Trimethyl-3-(5-hexylsulfonyl-1,3,4-thiadiazol-2-yl) urea | 3.0 | — | 10 | — | — | — | 10 | 10 | 10 | 0 | 0 | 0 | 0 | 0 | 0 | 0 |
| 4. 1,1,3-Trimethyl-3-(5-heptysulfonyl-1,3,4-thiadiazol-2-yl) urea | 3.0 | — | 10 | — | — | 10 | — | 10 | 10 | 0 | 0 | — | 0 | 0 | 0 | 0 |
| 5. 1,1,3-Trimethyl-3-(5-butylsulfinyl-1,3,4-thiadiazol-2-yl) urea | 1.0 | — | 10 | — | — | — | 10 | 10 | — | 0 | 0 | 0 | 0 | 0 | 0 | 0 |
| 6. 1,1,3-Trimethyl-3-(5-pentylsulfinyl-1,3,4-thiadiazol-2-yl) urea | 1.0 | 10 | 10 | — | — | 10 | 10 | 10 | — | 0 | 0 | 0 | 0 | 0 | 0 | 0 |
| 7. 1,1,3-Trimethyl-3-(5-hexylsulfinyl-1,3,4-thiadiazol-2-yl) urea | 3.0 | 10 | 10 | — | — | — | — | 10 | — | 0 | 0 | 0 | 0 | 0 | 0 | 0 |
| 8. 1,1,3-Trimethyl-3-(5-heptylsulfinyl-1,3,4-thiadiazol-2-yl) urea | 1.0 | 10 | — | — | — | — | — | 10 | 10 | 1 | 0 | 0 | 1 | 0 | 0 | 1 |
| 9. 1,1,3-Trimethyl-3-(5-isobutylsulfonyl-1,3,4-thiadiazol-2-yl) urea | 0.3 | — | 10 | 10 | 10 | 10 | 10 | 10 | — | 0 | 0 | 0 | 0 | 0 | 0 | 0 |
| 10. 1,1,3-Trimethyl-3-(5-ethylbutylsulfonyl-1,3,4-thiadiazol-2-yl) urea | 1 | — | 10 | 10 | 10 | 10 | 10 | 10 | — | 0 | 0 | 0 | 0 | 0 | 0 | 0 |
| 11. 1,1,3-Trimethyl-3-(5-isopentylsulfonyl-1,3,4-thiadiazol-2-yl) urea | 1 | 10 | 10 | 10 | 10 | 10 | 10 | 10 | — | 0 | 0 | 0 | 0 | 0 | 0 | 0 |
| 12. 1,1,3-Trimethyl-3-(5-ethylpentyl) sulfonyl-1,3,4-thiadiazol-2-yl) urea | 1 | 10 | 10 | 10 | 10 | 10 | 10 | 10 | — | 0 | 0 | 0 | 0 | 0 | 0 | 0 |
| 13. 1,1,3-Trimethyl-3-(5-(1-methylpropyl)-sulfonyl-1,3,4-thiadiazol-2-yl) urea | 0.3 | — | 10 | — | — | 10 | 10 | 10 | — | 0 | 0 | 0 | 0 | 0 | 0 | 0 |

-continued

| Agent according to invention | Quantity used kg eff. subst./ha | A | B | C | D | E | F | G | H | I | J | K | L | M | N | O |
|---|---|---|---|---|---|---|---|---|---|---|---|---|---|---|---|---|
| 14. 1-Methyl-1-(5-trifluoromethyl-1,3,4-thiadiazol-2-yl)-3-methyl urea | 1.0 | — | 3 | 3 | 3 | 3 | 0 | 8 | 0 | 0 | 0 | 0 | 0 | 0 | 0 | 0 |
| 15. 1,1,3-Trimethyl-3-(5-ethylsulfonyl-1,3,4-thiadiazol-2-yl) urea | 1.0 | 4 | 1 | 1 | 1 | 1 | 1 | 8 | 0 | 0 | 0 | 0 | 0 | 0 | 0 | 0 |
| 16. 1,1,3-Trimethyl-3-(5-n-propyl-sulfinyl-1,3,4-thiadiazol-2-yl) urea | 1.0 | 8 | 6 | 6 | 4 | — | — | — | 0 | 0 | 0 | 0 | 0 | 0 | 0 | 0 |
| 17. 1,1,3-Trimethyl-3-(5-isopropyl-sulfinyl-1,3,4-thiadiazol-2-yl) urea | 1.0 | 6 | 6 | 4 | 4 | 5 | — | 7 | 0 | 0 | 0 | 0 | 0 | 0 | 0 | 0 |
| 18. 1,1,3-Trimethyl-3-(5-ethylsulfinyl-1,3,4-thiadiazol-2-yl) urea | 1.0 | 3 | 2 | 1 | 0 | 1 | 2 | 5 | 0 | 0 | 0 | 0 | 0 | 0 | 0 | 0 |
| Untreated | | | | | | | | | | | | | | | | |

0 = totally destroyed
10 = not damaged
A = Peanut
B = Corn
C = Wheat
D = Barley
E = Rice
F = *Sorghum sativum*
G = Potato
H = Soybean
I = *Stellaria media*
J = *Matrisaria chamomilla*
K = *Lanium amplexicaule*
L = *Contaurea cyanus*
M = *Amaranthus retroflexus*
N = *Sinapis sap.*
O = *Senecio Vulgaris*

EXAMPLE 5

In a field test, repeated twice, plots of loamy sand with potatoes were treated with the agents listed in the table in the pre-emergence phase. The agent was sprayed as an aqueous suspension at 500 liters/ha, the quantity used being reduced continuously from 2.0 kg effective substance/ha to 0.0 kg effective substance/ha.

Six weeks after the treatment, the plots were practically weed free in the dose range between 2 kg and 0.3 kg effective substance/ha at full protection of the potatoes, while the untreated control plots showed extremely heavy growth of *Polygonum lapathifolium, Thiaspi arvense, Chenopodium album* and *Matricaria inodora*. An evaluation after a total of 8 weeks gave a still better effect in that the treated plots were practically weed free already from 0.2 kg effective substance per ha on. The potatoes showed no damage.

In the following table are stated the average values of the minimum quantities necessary for a very good weed effect.

| Agent according to invention | Minimum dose 6 weeks after treatment | Minimum dose 8 weeks after treatment |
|---|---|---|
| 1,1,3-Trimethyl-3-(5-butylsulfonyl-1,3,4-thiadiazol-2-yl) urea | 0.3 kf eff. substance/ha | 0.2 kg eff. substance/ha |

EXAMPLE 6

In another field test, repeated twice, on humus-rich sand for potatoes the agents listed in the table were applied in pre-emergence procedure with decreasing quantity, suspended in 500 liter of water/ha.

At the time of the first evaluation, untreated sections were heavily weed-covered with Chenopodium album, Spergula arvensis and Polygonum convolvulus with soil coverage of 40%. The evaluation occurred 6 and 10 weeks after application by determination of the threshold values for crop tolerance and weed effect. In the following table are stated the minimum doses for almost complete absence of weeds of each compound as well as the selectivity indexes calculated from these values. From this, the superior selectivity of the compound used according to the invention is evident.

| Agent according to invention | Minimum dose for very good weed effect | | Selectivity index | |
|---|---|---|---|---|
| | 6 weeks after application | 10 weeks after application | 6 weeks after application | 10 weeks after application |
| 1. 1,1,3-trimethyl-3-(5-n-butyl-sulfonyl-1,3,4-thiadiazol-2-yl) urea | 0.55 kg/ha | 0.2 kg/ha | 3.4 | 9.5 |
| 1. Comparison agent | | | | |
| 2. 1,1,3-Trimethyl-3-(5-n-propyl-sulfinyl-1,3,4-thiadiazol-2-yl) urea | 0.4 kg/ha | 0.5 kg/ha | 4.2 | 3 |
| 3. 1,1,3-Trimethyl-3-(5-isopropyl-sulfinyl-1,3,4-thiadiazol-2-yl) urea | 0.4 kg/ha | 0.3 kg/ha | 2.5 | 3 |
| 4. 1,1,3-Trimethyl-3-(5-ethyl-sulfonyl-1,3,4-thiadiazol-2-yl) urea | 0.18 kg/ha | 0.1 kg/ha | 3.4 | 3.5 |
| 5. N-(4-bromophenyl)-k'-methyl-N'-methoxy urea | 0.8 kg/ha | 0.8 kg/ha | 5 | 4.8 |

EXAMPLE 7

On a stand of potatoes, 1,1,3-Trimethyl-3-(5-n-butyl-sulfonyl-1,3,4-thiadiazol-2-yl) urea as well as 1,1,3-Trimethyl-3-(5-ethylsulfonyl-1,3,4-thiadiazol-2-yl) urea was sprayed in decreasing quantity, suspended in 500 liters water/ha, in the post-emergence phase of growth.

At the time of treatment the potato plants had developed 6 to 10 leaves. The heavy weed growth consisted mainly of *Chenopodium album* and *Polygonum convolvulus*, which had developed 2 to 10, and respectively, 2 to 4 true foliage leaves. Because of the weeds being shielded by the potato plants in spraying, only relatively high doses had achieved an almost 100% weed destruction. The table gives the threshold value for weed effect and the selectivity index, evaluation 4 weeks after application. Yet the compound, according to the invention, proved to be selective, while the known compound was no longer so under these more difficult conditions.

| Compound according to invention | Minimum dose for very good weed effect | Selectivity index |
| --- | --- | --- |
| 1,1,3-Trimethyl-3-(5-n-butyl-sulfonyl-1,3,4-thiadiazol-2-yl) urea | 1.1 kg/ha | >1.8 |
| Comparison agent | | |
| 1,1,3-Trimethyl-3-(5-ethylsulfonyl-1,3,4-thiadiazol-2-yl) urea | 0.6 kg/ha | 0.5 |

EXAMPLE 8

In a field test the compounds set forth in the following table were applied in decreasing amounts to potato plants in humus sand while in the pre-emergent state. The field was strongly infested with weeds such as *Chenopodium album, Thlaspi arvenense*, Matricaria spp., and Polygonum spp. (ground area covered=40%). About 6 weeks after application threshold values for crop tolerance and weedicidal activity were evaluated. Table below shows the minimum dosage for substantially complete freedom from weeds and the selectivity index indicating compatibility to crop for a compound of this invention and a dimethyl analog.

TABLE

| Compound | Minimum dosage for substantially complete weedicidal activity 6 weeks after application | Selectivity Index 6 weeks after Application |
| --- | --- | --- |
| 1,1,3-Trimethyl-3-(5-n-butylsulfonyl-1,3,4-thiadiazol-2-yl) urea | 0.15 kg/ha | 20 |
| Comparison compound | | |
| 1,3,-Dimethyl-3-(5-n-butyl-sulfonyl-1,3,4-thiadiazol-2-yl) urea | 0.84 kg/ha | 3.57 |

EXAMPLE 9

A potato field was sprayed, in post-emergence, with 1,1,3-trimethyl-3-(5-n-butylsulfonyl-1,3,4-thiadiazol-2-yl) urea as well as 1,3,-dimethyl-3-(5-n-butylsulfonyl-1,3,4-thiadiazol-2-yl) urea suspended in 500 liters water/ha at a decreasing rate.

At the time of treatment the potato plants had developed 6 to 10 leaves. The heavy weed contamination consisted mainly of *Solanum nigrum, Stellaria media*, Galeopsis spp., and *Polygonum concolculus*, which had developed 2 to 10 true leaves. The table shows the threshold values for weedicidal activity and the selectivity index (evaluation took place 4 weeks after application). The compound according to the invention proved selective, the comparison compound was not.

| Compound according to Invention | Minimum dosage for very good weedicidal activity | Selectivity Index |
| --- | --- | --- |
| 1,1,3-Trimethyl-3-(5-n-butylsulfonyl-1,3,4-thiadiazol-2-yl) urea | 0.24 kg/ha | 8.5 |
| Comparison compound | | |
| 1,3,-Dimethyl-3-(5-n-butyl-sulfonyl-1,3,4-thiadiazol-2-yl) urea | 1.95 kg/ha | 0.92 |

What is claimed:

1. A method of preventing weed growth in potato plant cultures, comprising applying to said cultures a composition consisting essentially of a compound of the formula

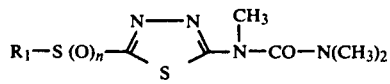

wherein $R_1$ is an alkyl radical of 4 to 8 carbon atoms, and
n is 1 or 2, in an amount sufficient to provide between about 0.1 to 5 kg of said compound per hectare, whereby weed growth is prevented without causing substantial damage to said potato plants.

2. A method as defined in claim 1, wherein the compound is 1,1,3-trimethyl-3-(5-butylsulfinyl-1,3,4-thiadiazol-2-yl) urea.

3. A method as defined in claim 1, wherein the compound is 1,1,3-trimethyl-3-(5-butylsulfonyl-1,3,4-thiadiazol-2-yl) urea.

4. A method as defined in claim 1, wherein the compound is 1,1,3-trimethyl-3-(5-pentylsulfinyl-1,3,4-thiadiazol-2-yl) urea.

5. A method as defined in claim 1, wherein the compound is 1,1,3-trimethyl-3-(5-hexylsulfinyl-1,3,4-thiadiazol-2-yl) urea.

6. A method as defined in claim 1, wherein the compound is 1,1,3-trimethyl-3-(5-heptylsulfinyl-1,3,4-thiadiazol-2-yl) urea.

7. A method as defined in claim 1, wherein the compound is 1,1,3-trimethyl-3-(5-pentylsulfonyl-1,3,4-thiadiazol-2-yl) urea.

8. A method as defined in claim 1, wherein the compound is 1,1,3-trimethyl-3-(5-hexylsulfonyl-1,3,4-thiadiazol-2-yl) urea.

9. A method as defined in claim 1, wherein the compound is 1,1,3-trimethyl-3-(5-heptylsulfonyl-1,3,4-thiadiazol-2-yl) urea.

* * * * *